(12) United States Patent
Ogawa et al.

(10) Patent No.: US 7,005,784 B2
(45) Date of Patent: Feb. 28, 2006

(54) ELECTRODE APPARATUS FOR PREVENTING CRACKING OF THE ELECTRODE AND INSULATING LAYERS

(75) Inventors: Tatsuya Ogawa, Tokyo (JP); Saori Takahashi, Tokyo (JP); Yasushi Fuchita, Tokyo (JP); Kenji Mori, Tsukuba (JP); Naruhito Higo, Tsukuba (JP)

(73) Assignees: Kyodo Printing Co., Ltd., Tokyo (JP); Hisamitsu Pharmaceutical Co., Inc., Saga (JP)

( * ) Notice: Subject to any disclaimer, the term of this patent is extended or adjusted under 35 U.S.C. 154(b) by 262 days.

(21) Appl. No.: 10/650,195

(22) Filed: Aug. 27, 2003

(65) Prior Publication Data

US 2005/0174029 A1 Aug. 11, 2005

(30) Foreign Application Priority Data

Aug. 29, 2002 (JP) .............................. 2002-249858

(51) Int. Cl.
*H01J 1/00* (2006.01)

(52) U.S. Cl. ...................................... 313/326; 313/310

(58) Field of Classification Search ................ 313/309, 313/336, 351, 311, 310
See application file for complete search history.

(56) References Cited

U.S. PATENT DOCUMENTS

| 4,407,871 A | 10/1983 | Eisfeller ....................... 428/31 |
| 5,224,265 A * | 7/1993 | Dux et al. ..................... 29/852 |
| 6,887,967 B1 * | 5/2005 | Ichinose et al. ............. 528/170 |

FOREIGN PATENT DOCUMENTS

| EP | 1 177 814 A1 | 2/2002 |
| JP | 2002047029 | 2/2002 |

* cited by examiner

*Primary Examiner*—Joseph Williams
(74) *Attorney, Agent, or Firm*—Frommer Lawrence & Haug LLP; Ronald R. Santucci

(57) ABSTRACT

It is an object of the invention to prevent not only cracking but also blocking of an electrode layer 20 and an electrically insulating layer 30, particularly the electrically insulating layer 30, which is formed on a base film 10. An electrode apparatus comprises a base film 10 for defining a recess 50 at the inner periphery of a bending part 500, and an electrode layer 20 and an electrically insulating layer 30 which are pattern formed on the base film 10. The electrode layer 20 crosses the bending part 500 from the inside of the recess 50 to the outside. The electrically insulating layer 30 covers the upper part of the electrode layer 20 in the vicinity of the bending part 500. A resin composition obtained by admixing a low Tg resin having a glass transition temperature equal to 25 degrees C. or lower and a high Tg resin having a higher glass transition temperature (for example, 40 degrees C. or higher) than that of the low Tg resin is used as a dielectric of the electrically insulating layer 30.

8 Claims, 3 Drawing Sheets

ELECTRODE APPARATUS FOR PREVENTING CRACKING OF THE ELECTRODE AND INSULATING LAYERS

This application claims priority benefits from Japanese Patent Application No. 2002-249858 filed Aug. 29, 2002.

FIELD OF THE INVENTION

This invention relates to an electrode apparatus for biocompatible electrode apparatus which can be used in the medical field such as treatment and diagnosis of illness, and more particularly to an electrode apparatus which can prevent the occurrence of cracking of an electrode layer and an electrically insulating layer which are elements composing the electrode apparatus.

BACKGROUND OF THE INVENTION

The iontophoresis (Acta Dermatol venereol, vol. 64, p. 93, 1984) and the electropolation (National Patent Publication No. H03-502416, Proc. Acad. Sci. USA, vol. 90, p. 10504 through 10508, 1993) teach a treatment method in which chemicals and physiologically active substance are introduced into a living body from the skin and the mucous membrane by using electric energy. There is also known a method, in which a substance to be diagnosed is extracted from a living body so that the condition of a disease can be observed based on the same principle as above (Nature Medicine, vol. 1, p. 1198 through 1201, 1995). The electrode apparatus is necessarily used in these methods for applying the electric energy to the substances.

Japanese Patent Application Laid-Open No. 2000-316991 discloses an idea in which an electrode apparatus of this type is such designed as to be disposable after use while an external power supply such is designed as to be repeatedly used. The disposable electrode apparatus basically comprises a bending part, a base film including a first and a second part having a difference in height by serving the bending part as a boundary, an electrode layer formed on the base film in such a manner as to cross the bending part and fully extend over the first and second parts which are different in height, and an electrically insulating layer formed on the electrode layer at its selective region including the bending part. An electrode apparatus of this type essentially includes a bending part for the purpose, among others, of defining a receptacle part (dent or recess) for receiving an electrolytic substance on its inner periphery.

PRECEDING RELATED PROPOSAL

A serious technical problem involved in the electrode apparatus having a bending part of the type mentioned above is to effectively prevent the occurrence of cracking of the electrode layer and the electrically insulating layer which readily occurs in the vicinity of the bending part. Cracking of the electrode layer is liable to cause an electric cut-off, and cracking of the electrically insulating layer is liable to expose the electrode layer, thus resulting in leakage of electricity. Therefore, it is important to effectively prevent the occurrence of such cracking. As a result of extensive search and investigation as for what causes cracking of the electrode layer and the electrically insulating layer, they, the inventors of the present invention, found that the difference in elongation occurrable between the electrode layer and the electrically insulating layer formed on the base film when external force is applied thereto is a main cause of cracking.

The main external force applicable to the electrode apparatus is a compressive force occurrable when the bending part is shaped. In addition, the force applicable when the electrode apparatus is used can also be counted as such external force.

Based on such extensive search and investigation, the present inventors have previously proposed an invention under Japanese Patent Application No. 2002-47029 (filing date: Feb. 22, 2002). In that preceding application, in order to allow the electrically insulating layer to be flexibly elongated in accordance with the elongation of the electrode layer and the base film when an external force is applied thereto, a resin material having a glass transition temperature equal to 25 degrees C. or lower, preferably 0 degrees or lower, and more preferably −20 degrees or lower is used as a dielectric which constitutes the electrically insulating layer.

DISCLOSURE OF THE INVENTION

Problem to be Solved by the Invention

The difference in elongation among the base film, the electrode layer and the electrically insulating layer at the bending part will exert a greater influence on the electrically insulating layer which is located at a higher position. In order to prevent the occurrence of cracking of the electrically insulating layer more positively, it is preferable that a resin having such a lower glass transition temperature is used as a dielectric which constitutes the electrically insulating layer. However, it became newly clear that when such a resin as having a lower glass transition temperature is used, there is a possibility that a phenomenon, i.e., blocking, occurs in which adjacent electrode apparatuses are adhered to each other. Blocking can be hindrance in handling a plurality of electrode apparatuses, particularly when electrode apparatuses are to be manufactured on a mass production basis.

It is, therefore, an object of the present invention to provide a technique capable of preventing the occurrence of cracking of an electrode layer and an electrically insulating layer, particularly the electrically insulating layer formed on a base film, and also capable of preventing the occurrence of blocking.

Means for Solving the Problem and Preferred Mode of the Invention

This invention is based on such finding that when two kinds of resins having a different glass transition temperature are blended (mixed), the blended resin composition has such characteristics as to independently show the respective glass transition temperatures of the two kinds of blended resins. By using a resin material having a glass transition temperature equal to 25 degrees C. or lower, preferably 0 degrees or lower, and more preferably −20 degrees or lower as in the preceding proposal, the electrically insulating layer is increased in flexibility, so that the occurrence of cracking can be prevented. Moreover, by using a resin material having a glass transition temperature equal to room temperature or higher, and preferably 40 degrees C. or higher as a dielectric which constitutes the electrically insulating layer, the occurrence of blocking can be prevented effectively. So, in the present invention, based on the above-mentioned finding, a resin composition which includes, at least, a low Tg resin having a glass transition temperature equal to or lower than 25 degrees C., and a high Tg resin having a higher glass transition temperature than that of the low Tg resin is used as a dielectric which constitutes the electrically insulating layer. The expression "which includes, at least," refers to the inclusion of, in addition to resin, a solvent for dissolving the resin, and the known additives such as silica and bentonite. Moreover, it also means that other resins can be admixed in view of cost reduction and excellent suitability for coating. Other resins can be admixed in a small amount, for example, 3 wt. % or less, within a range not prejudiciary to the object of the present invention.

As a dielectric which constitutes the electrically insulating layer, various resin materials of electrically insulating properties including a copolymer of polyester-series, polyethylene-series, polypropylene-series, acryl-series, polyimide-series, or the like can be used. A low Tg resin and a high Tg resin having a predetermined transition temperature can be suitably selected from them and used. Among them, thermoplastic saturated copolymer polyester resin is particularly preferable. At the time for blending the low Tg resin and the high Tg resin together, it is preferable to blend the resins of the same series in view of their compatibility, etc. However, resins of different kinds can also be blended without any problem. As long as the resins blended together can be used for coating the electrically insulating layer, those resins are applicable to the present invention.

As for the base film itself, a member obtained by laminating the plastic film and the metal film as in the laid-open publication of Japanese Patent Application Laid-Open No. 2000-316991 can widely be applied. In order to have the electrode apparatus itself deformed to some extend so as to be intimately contacted with the skin in use, the base film is preferably be readily bent by hand and the bending state can be retained. In this respect, as shown in Japanese Patent Application Laid-Open No. H11-54855, both the plastic film and metal film should be designed to have a thickness of 10 to 200 $\mu$m and the layered structure should be designed by taking into consideration of the restoring characteristics for restoring the bending state of the plastic film and the shape retaining force for retaining the bending state of the metal film. It is a boundary condition that in case the thickness of the metal film is 1, the ratio of the thickness of the plastic film is 2. When the cost factor, etc. are taken into consideration besides the above-mentioned shape retainability, the plastic film and the metal film are preferably 30 through 100 $\mu$m in thickness. Particularly preferably, the respective layers are made equal in thickness and set to 40 through 80 $\mu$m. As a material of the plastic film, polyethylene terephthalate having excellent electrically insulating properties is suitable. Besides this material, polyolefin-series such as polyimide, polyethylene and polypropylene, or polyester-series as represented by polyethylene naphthalate can also be used. On the other hand, as a material of the metal film, aluminium or its alloy is suitable. Besides this material, copper, zinc, silver, gold and lead, or alloy thereof can also be used. The most suitable form of lamination of the base film is a sandwiched form obtained by sandwiching the metal film with plastic film at its upper and lower surfaces.

The electrode apparatus having a bending part is obtained by forming an electrode layer on one surface of the base film, and then forming an electrically insulating layer in such a manner as to cover at least a part of the electrode layer, then forming a bending part (normally, a dent or recess is defined such that its inner periphery serves as a receptacle part) by cold pressing in order to avoid the occurrence of thermal breaking of the electrode layer and the electrically insulating layer and thereafter punch-working the base film into a predetermined shape. Therefore, the electrode apparatus having a bending part generally includes a first part (dent) having a small height and a second part (electrode terminal part) having a large height part with the bending part disposed therebetween. In order to form an electrode layer and an electrically insulating layer on the base film, printing such as screen printing and gravia is suitably applied. Particularly, by applying the screen printing, the thickness can easily be controlled and in addition, a pattern can correctly be drawn by printing. As a material of the electrode layer, various kinds of electrode materials can be applied. In case the electrode layer is formed by printing, for example, paste ink (particularly, one which is readily elongated such as ink chiefly composed of carbon and readily elongated) can be used. Since the electrically insulating layer is provided in such a manner as to prevent the electrode part from directly contacting the skin, it covers the electrode layer in such a manner as to necessarily include the bending part. Accordingly, the thickness of the electrically insulating layer should be set to, for example, 0.5 $\mu$m through 100 $\mu$m and more preferably to 1 $\mu$m through 30 $\mu$m, so that effective electrically insulating properties can be maintained considering the elongation due to the pressing.

PREFERRED EMBODIMENT OF THE INVENTION THROUGH EXPERIMENT

FIRST EXPERIMENTAL EXAMPLE

Figure 1:
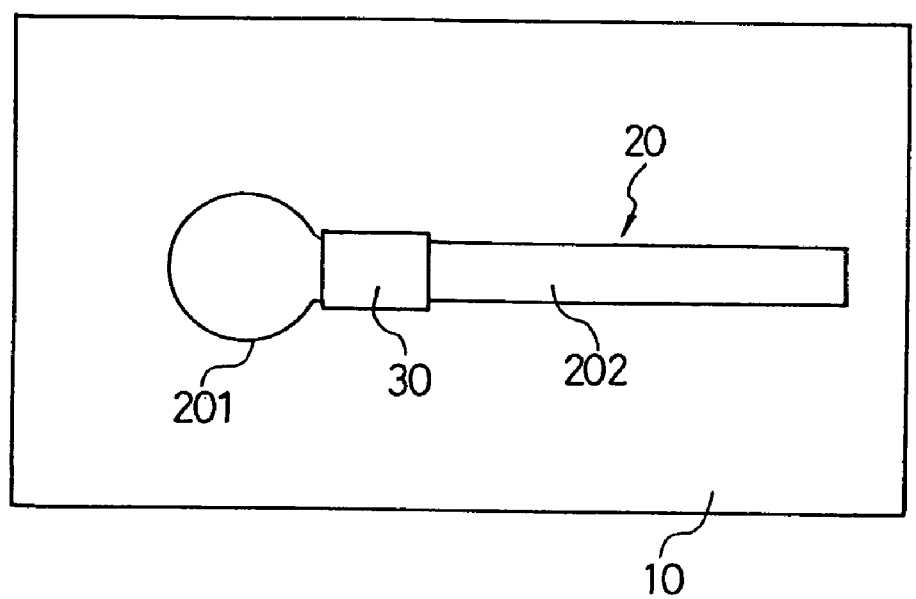
FIG. 1 is a top view of an electrode apparatus which is in the process of being manufactured.
Figure 2:
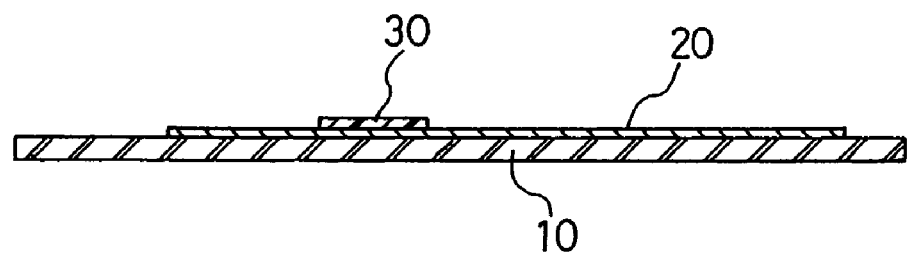
FIG. 2 is a side sectional view of FIG. 1.
Figure 3:
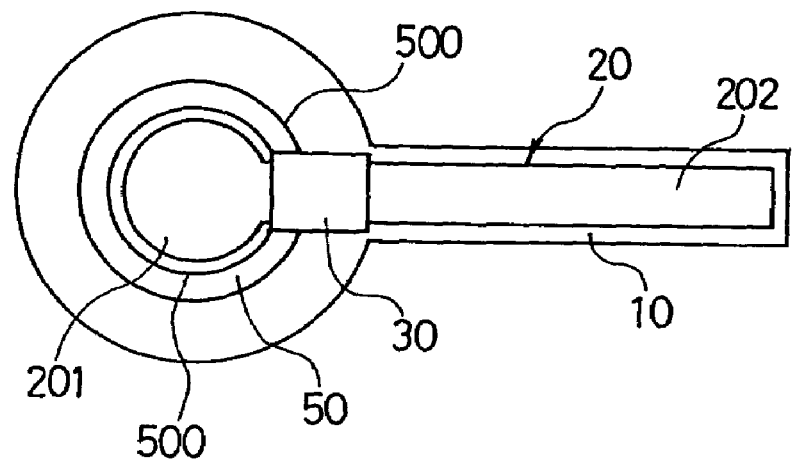
FIG. 3 is a top view showing a state of the electrode apparatus after it is subjected to molding treatment and punching treatment.
Figure 4:
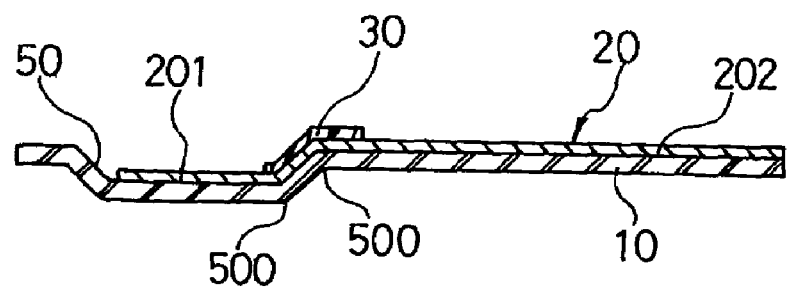
FIG. 4 is a side sectional view of FIG. 3.

The present invention was applied to an aluminum laminated cup-type electrode apparatus having a recess (dent) and confirmed the occurrence of cracking and blocking of the electrically insulating layer. FIG. 1 is a top view showing a printed pattern and FIG. 2 is a side sectional view thereof. FIG. 3 is a top view of one form of the electrode apparatus after bending the base film so as to define a bent and then punch-working the same. FIG. 4 is a side sectional view of FIG. 3. First, an aluminum laminated member was prepared which was obtained by laminating polyethylene terephthalate having a thickness of 25 $\mu$m on the entire surface of an aluminium plate having a thickness of 38 $\mu$m and this member was used as a base film 10. Then, an electrode layer 20 having a thickness of about 40 $\mu$m was formed on one surface of the electrically insulating polyethylene terephthalate on the base film 10 by screen printing using silver paste having a silver content of 90%. The electrode layer 20 includes a circular part 201 and a rectangular part 202 which is partly overlapped with the circular part 201. After the electrode layer 20 was dried, several kinds of dielectrics having a thickness of 15 $\mu$m were coated thereon in such a manner as to partly cover the rectangular part 202 by screen printing so that a square electrically insulating layer 30 was formed. As the several kinds of dielectrics, resin was used which was obtained by blending two kinds of resins one of which was 85 degrees C. in glass transition temperature Tg and the other of which was −29 degrees C. At the time of blending, one of the resins was changed in part, such as 85 parts, 75 parts, 65 parts, 50 parts and 25 parts, and in addition, for the purpose of comparison, resins of 100 parts and 0 parts were also prepared. In other words, resins having a glass transition temperature Tg of 85 degrees C. and −29 degrees C., which were each used alone, were also prepared. The term "parts" used here refers to weight %. After the electrically insulating layer 30 was printed, a dent 50 was formed by compression molding and the occurrence of cracking at the bending part 500 on the periphery of the dent 50 (particularly the occurrence of cracking of the electrically insulating layer 30) was confirmed. As a resin which constitutes the electrically insulating layer 30, thermoplastic saturated copolymer polyester was used.

Figure 5:
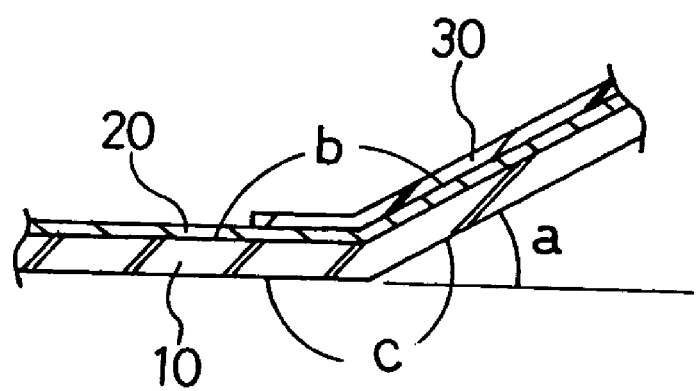
FIG. 5 is a partly side sectional view for explaining the bending angle of a bending part.

The presence (Yes)/absence (No) of cracking of the electrically insulating layer 30 was determined by inferior insulation verification test of the electrode apparatus. The test is carried out in the following manner. First, a test circuit is constructed by an anode (Ag), an electrolytic solution (physiological solution of sodium chloride), a cathode (AgCl) and a constant current source. When an electric current is supplied to this circuit, Ag is reacted with minus ion of Cl so that AgCl is generated. If cracking is present at the electrically insulating layer 30 at that time, the electrolytic solution is infiltrated therein to generate AgCl. When such AgCl is generated, the anode is changed in color from silver white to brown so that the occurrence of cracking can be visually recognized (this cannot be recognized at the cathode). With respect to blocking, its presence (Yes)/absence (No) was determined by overlapping the electrode apparatuses and exerting a load of 1 kg/cm$^2$ for 24 hours at 40 degrees C. In order to put an electrolytic substance into the dent 50, the bending angle a (see FIG. 5) of the bending part 500 at the periphery of the dent 50 is normally set to 20 degrees through 90 degrees. With respect to the bending, the angle b at the inner side of the dent 50, i.e., on the side of the electrically insulating layer 30 is referred to as "the interior angle", and the angle c on the side of the base film 10 located opposite thereto is referred to as "the conjugate angle". Since the degree of bending affects the occurrence of cracking of the electrically insulating layer 30, two cases of the conjugate angles 230 degrees and 250 degrees were tested. Table 1 shows the result of the first experimental example.

TABLE 1

| | Tg 85 degrees C. | Tg −29 degrees C. | Conjugate Angle 230° | Conjugate Angle 250° | Blocking |
|---|---|---|---|---|---|
| Sample 1 | 100 parts | 0 parts | 10/10 | 10/10 | No |
| Sample 2 | 85 parts | 15 parts | 0/10 | 0/10 | No |
| Sample 3 | 75 parts | 25 parts | 0/10 | 0/10 | No |
| Sample 4 | 65 parts | 35 parts | 0/10 | 0/10 | No |
| Sample 5 | 50 parts | 50 parts | 0/10 | 0/10 | No |
| Sample 6 | 25 parts | 75 parts | 0/10 | 0/10 | Yes |
| Sample 7 | 0 parts | 100 parts | 0/10 | 0/10 | Yes |

(Occurrence number of cracking of the electrically insulating layer/total measured number)

The following things can be known from the result of Table 1. With respect to the sample 1 which is 100 parts of resin (high Tg resin) having a glass transition temperature of 85 degrees C., cracking occurs to all of the total measured number of 10. In case of the samples 2 through 6 in which the low Tg resin and the high Tg resin are blended together, as well as the sample 7 which is 100 parts of resin (low Tg resin) having a glass transition temperature of −29 degrees C., no cracking of the electrically insulating layer 30 can be seen. Accordingly, in order to prevent the occurrence of cracking of the electrically insulating layer 30, it is effective to include the low Tg resin having a low glass transition temperature as a dielectric of the electrically insulating layer 30 (first finding). On the other hand, in case of the samples 2 through 5 which have a large content of the high Tg resin, as well as the sample 1 which is 100 parts of high Tg resin, no blocking phenomenon can be seen. However, in case of the sample 7 which is 100 parts of the low Tg resin and the sample 6 which has a large content of the low Tg resin, the blocking phenomenon can be seen. This indicates that in order to prevent the occurrence of blocking, it is effective to include a comparatively large amount of the high Tg resin having a high glass transition temperature as a dielectric of the electrically insulating layer 30 (second finding).

SECOND EXPERIMENTAL EXAMPLE

In order to more firmly make sure of the result of the first experimental test, the same experiment as in the first experimental example using polyester-series resin (merchandise name: ELITEL UE-3223, manufactured by Unitika K. K.) having a glass transition temperature of 1 degree C. as a low Tg resin, and further using the same polyester-series resin (merchandise name: ELITEL UE-9800, manufactured by Unitika K. K.) having a glass transition temperature of 85 degrees C. as in the first experimental example as a high Tg resin. Table 2 shows the result of the second experimental example.

TABLE 2

| | Tg 85 degrees C. | Tg 1 degree C. | Conjugate Angle 230° C. | Conjugate Angle 250° | Blocking | Fine cracking |
|---|---|---|---|---|---|---|
| Sample 8 | 100 parts | 0 parts | 10/10 | 10/10 | No | X |
| Sample 9 | 80 parts | 20 parts | 10/10 | 10/10 | No | X |
| Sample 10 | 60 parts | 40 parts | 0/10 | 0/10 | No | Δ |
| Sample 11 | 50 parts | 50 parts | 0/10 | 0/10 | No | ○ |
| Sample 12 | 40 parts | 60 parts | 0/10 | 0/10 | Yes | ○ |
| Sample 13 | 20 parts | 80 parts | 0/10 | 0/10 | Yes | ○ |
| Sample 14 | 0 parts | 100 parts | 0/10 | 0/10 | Yes | ○ |

(Occurrence number of cracking of the electrically insulating layer/total measured number)
○: No fine cracking has occurred
Δ: Fine cracking has slightly occurred
X: Fine cracking has occurred As apparent from Table 2, the occurrence of cracking of the electrically insulating layer 30 can be prevented by including a predetermined amount or more (more than 20 parts, and preferably 50 parts or more) of the low Tg resin having a glass transition temperature of 1 degree C. (samples 10 through 14) as a dielectric of the electrically insulating layer 30. This is the same as the first finding obtained through the first experimental example. Similarly, the occurrence of blocking can be prevented by including a predetermined amount or more (more than 50 parts) of the high Tg resin having a glass transition temperature of 85 degrees C. (samples 8 through 11) as a dielectric of the electrically insulating layer 30. This is the same as the second finding obtained through the first experimental example. When the results of the first and second experimental examples are compared with each other, from the view point of prevention of the occurrence of blocking, it is preferable to include the high Tg resin having a high glass transition temperature and to select a resin having a rather high glass transition temperature (for example, 1 degree C. resin is preferable to −29 degrees C. resin) as a low Tg resin to be blended having a low glass transition temperature (third finding). When taking into consideration of the result of the second experimental example in addition to the result of the first experimental example, in case of blending the low Tg resin having a glass transition temperature of −20 degrees C. or lower and the high Tg resin having a glass transition temperature of 65 degrees C. or higher together, it is known that the amount of the low Tg resin may be set to 1 through 50 weight parts.

THIRD EXPERIMENTAL EXAMPLE

So, investigation was further continued as to what kind of adverse effects are prevailed on cracking or blocking of the electrically insulating layer 30 by changing the glass transition temperature. The results are shown in Tables 3 and 4.

TABLE 3

|  | Resin Tg | Conjugate Angle 230° | Conjugate Angle 250° | Blocking |
|---|---|---|---|---|
| Sample 15 | Tg 85 degrees C. | 6/10 | 10/10 | No |
| Sample 16 | Tg 67 degrees C. | 4/10 | 10/10 | No |

TABLE 4

|  |  | Low Tg resin | | |
|---|---|---|---|---|
|  |  | −29 | −20 | 1 |
| High Tg resin | 40 | X | X | ◯ |
|  | 67 | Δ | Δ | ◯ |
|  | 85 | ◯ | ◯ | ◯ |

◯: No blocking has occurred
Δ: Blocking has slightly occurred
X: Blocking has occurred From the result of Table 3 regarding the resins having the glass transition temperatures of 85 degrees C. and 67 degrees C., it is known that the two resins are effective in preventing the occurrence of blocking but the resin having the lower glass transition temperature of 67 degrees C. than the resin having the higher glass transition temperature of 85 degrees C. seems to be more effective for the purpose of prevention of the occurrence of cracking of the electrically insulating layer 30. Moreover, it is known that the case having a smaller conjugate angle of 230 degrees C. is more effective than the case having a larger conjugate angle of 250 degrees C.

As a high Tg resin, thermoplastic saturated polyester-series resins (merchandise name: ELITEL UE-3216, manufactured by Unitika K. K.) having a glass transition temperature of 40 degrees C., (merchandise name: ELITEL UE-3200, manufactured by Unitika K. K.) having a glass transition temperature of 67 degrees C., and (merchandise name: ELITEL UE-9800, manufactured by Unitika K. K.) having a glass transition temperature of 85 degrees C. were used, and as a low Tg resin, thermoplastic saturated polyester-series resins (merchandise name: ELITEL UE-3401, manufactured by Unitika K. K.) having a glass transition temperature of −29 degrees C., (merchandise name: ELITEL UE-3400, manufactured by Unitika K. K.) having a glass transition temperature of −20 degrees C., and (merchandise name: ELITEL UE-3223, manufactured by Unitika K. K.) having a glass transition temperature of 1 degree C. were used. The high Tg resin and the low Tg resin were blended together at the ratio of 1:1. The result of blocking test is shown in Table 4. The result of Table 4 verifies the third finding. From the view point of prevention of the occurrence of blocking, it is preferable to use a resin having a higher glass transition temperature as a high Tg resin. Also, as a low Tg resin, it is preferable to use a resin having a higher glass transition temperature (for example, resin of approximately 0 degree C.) within the range not prejudiciary to prevention of the occurrence of cracking of the electrically insulating layer. Moreover, Table 4 teaches that in case a low Tg resin having a glass transition temperature of 1 degree C. or lower and a high Tg resin having a glass transition temperature of 40 degrees C. or higher are to be blended together, the blending ratio is preferably set to approximately 1:1 (for example, 45/55 through 55/45). In the experiments of Table 4, totally no fine cracking of the electrically insulating layer has occurred.

What is claimed is:

1. An electrode apparatus comprising a base film having a bending part, an electrode layer formed in a region including said bending part on said base film, and an electrically insulating layer formed in a selected region including said bending part on said electrode layer,
wherein a dielectric, which constitutes said electrically insulating layer, is a resin composition which includes, at least, a low Tg resin having a glass transition temperature equal to or lower than 25 degrees C., and a high Tg resin having a higher glass transition temperature than that of said low Tg resin.

2. An electrode apparatus according to claim 1, wherein said base film includes a first part and a second part having a difference in height with reference to said bending part, said electrode layer is formed over said first and second parts.

3. An electrode apparatus according to claim 1, wherein said resin composition exhibits both the low and high glass transition temperature characteristics which said low and high Tg resins have, respectively.

4. An electrode apparatus according to claim 1, wherein the glass transition temperature of said high Tg resin is 40 degrees C. or higher.

5. An electrode apparatus according to claim 1, wherein said resin composition has both the functions for preventing cracking liable to give damage to said electrically insulating layer by external force and for preventing blocking.

6. An electrode apparatus according to claim 1, wherein said base film is composed of a laminated member obtained by laminating a plastic film and a metal film together, said laminated member can easily be bent by hand and the bending state of said laminated member can be retained.

7. An electrode apparatus according to claim 1, wherein said bending part defines at a periphery thereof a receptacle part which receives therein a gel containing an electrolyte.

8. An electrode apparatus according to claim 1, wherein said electrically insulating layer has a thickness of 0.5 μm to 100 μm.

* * * * *